United States Patent [19]

Haltrich

[11] Patent Number: 4,733,409
[45] Date of Patent: Mar. 22, 1988

[54] CASSETTE RECEPTACLE FOR X-RAY FILM CASSETTES

[75] Inventor: Manfred Haltrich, Heroldsbach, Fed. Rep. of Germany

[73] Assignee: Siemens Aktiengesellschaft, Berlin and Munich, Fed. Rep. of Germany

[21] Appl. No.: 802,245

[22] Filed: Nov. 27, 1985

[30] Foreign Application Priority Data

Jan. 11, 1985 [DE] Fed. Rep. of Germany ... 8500625[U]

[51] Int. Cl.⁴ ............................................. G03B 41/16
[52] U.S. Cl. ................................................... 378/167
[58] Field of Search .............................. 378/167, 181

[56] References Cited

U.S. PATENT DOCUMENTS 3,991,316 11/1976 Schmidt et al. .
4,060,733 11/1977 Franke et al. .
4,132,897 1/1979 Ohlson et al. ....................... 378/167
4,162,407 7/1979 Sharp .................................. 378/167
4,247,778 1/1981 Waerve .......................... 378/181 X
4,612,661 9/1986 Dallas .............................. 378/167 X

FOREIGN PATENT DOCUMENTS 1614956 12/1970 Fed. Rep. of Germany .
2449708 4/1976 Fed. Rep. of Germany .

*Primary Examiner*—Robert C. Watson
*Attorney, Agent, or Firm*—Hill, Van Santen, Steadman & Simpson

[57] ABSTRACT

The invention provides a receptacle for x-ray film cassettes which is composed of a one-piece plastic part provided with molded parts which center a radiation detector in the interior of the receptacle either in a longitudinal or transverse orientation.

5 Claims, 1 Drawing Figure

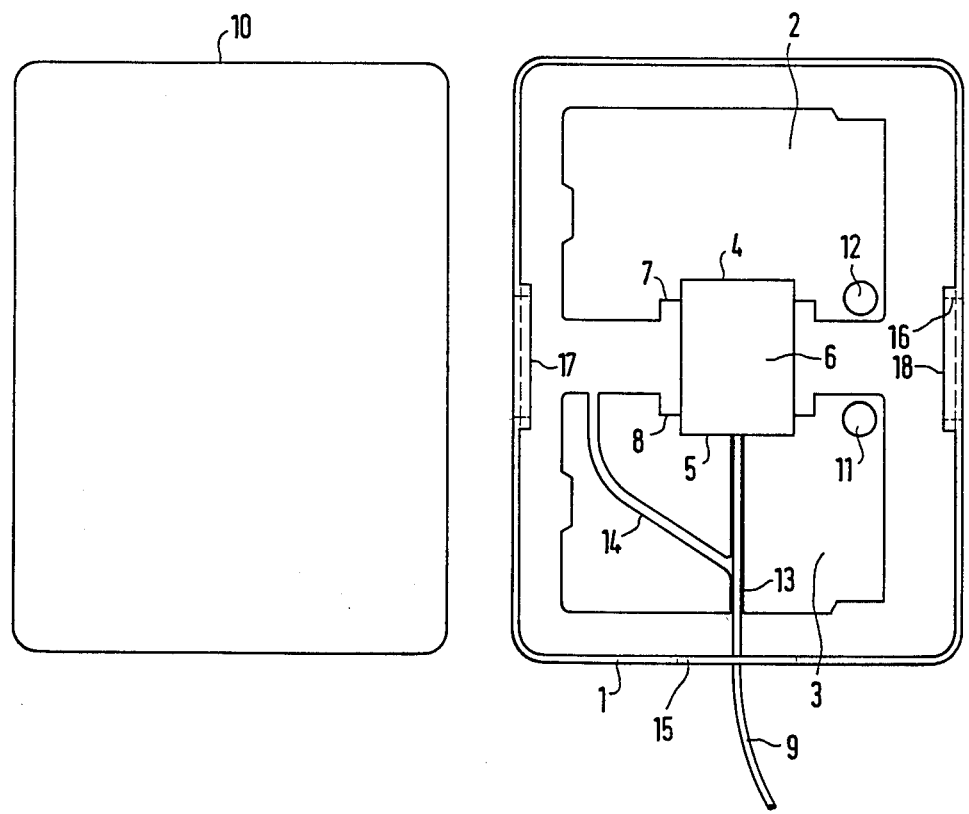

CASSETTE RECEPTACLE FOR X-RAY FILM CASSETTES

BACKGROUND OF THE INVENTION

1. Field of the Invention

The invention relates to a cassette receptacle for x-ray film cassettes including a radiation detector lying in the inside thereof.

2. Description of the Prior Art

German OS No. 24 49 708 discloses a cassette receptacle of this type. This cassette receptacle is composed of a housing into which the x-ray film cassette can be inserted and in which the radiation detector is seated with the assistance of a displaceable bar. The adjustment of the radiation detector thereby is accomplished with the assistance of scales on the bar and at the cassette housing.

An individual adjustment of the radiation detector is not always required in practice. It is frequently sufficient when the radiation detector lies in a specific position, particularly centrally behind the inserted film cassette.

SUMMARY OF THE INVENTION

An object of the invention is to fashion a cassette receptacle of the type initially cited such that, given a simple structure, the bearing of the radiation detector at a prescribed location is guaranteed.

This object is achieved in accord with the invention by a one-piece plastic part which is provided with molded portions mated to the shape of the radiation detector, these molded portions holding the radiation detector. Given the cassette receptacle of the invention, the radiation detector is placed in the molded portions of the cassette part accepting it, which are provided for this purpose, and is then fixed at the desired place behind the x-ray film cassette inserted thereover and latched in. The film cassette can be removed in a simple way when holes through which the film cassette can be manually pushed away are provided in the cassette receptacle.

The part accepting the radiation detector can thereby be a deep-drawn part.

The dimensions and weights of the cassette receptacle with cassette seated therein are not significantly greater than those of the cassette itself. Easy manipulation is thereby established. The manufacturing costs for the cassette receptacle are low.

BRIEF DESCRIPTION OF THE DRAWINGS

The invention shall be explained in greater detail below with reference to an exemplary embodiment shown in the drawing which is an exploded view of a film cassette and an open film cassette in plan view.

DESCRIPTION OF THE PREFERRED EMBODIMENTS

The drawing shows a cassette receptacle 1 which is formed by a one-piece drawn plastic part comprising molded parts 2, 3 which project inwardly proceeding from a floor of the cassette receptacle 1 and which, with the assistance of edges 4, 5, define a space for a radiation detector 6 in an upright format. The radiation detector 6 thereby fits precisely between the edges 4, 5. The radiation detector 6 can be inserted in transverse format when it is placed against the edges 7, 8. Its cable 9 can thereby be conducted past between the molded parts 2, 3 when it lies in transverse format or can also lie in a depression 13 of the molded parts 3 provided for this purpose, as shown in the drawing in the upright format. In transverse format, the cable 9 can also lie in a depression 14 of the molded part 3 when it proceeds from the left-hand side of the radiation detector 6.

After the radiation detector 6 has been placed in the desired position, the x-ray film cassette 10 is placed thereabove and is held by projections 17, 18 provided at the upper side of the cassette receptacle 1 which engage over the cassette 10.

A removal of the cassette 10 is possible in a simple fashion when slight pressure is exerted on the cassette through two openings 11, 12 in the floor of the cassette receptacle.

The insertion of the radiation detector 6 is possible through two fitting slots 15, 16 at the longitudinal sides of the cassette receptacle 1.

As is apparent from the foregoing specification, the invention is susceptible of being embodied with various alterations and modifications which may differ particularly from those that have been described in the preceeding specification and description. It should be understood that I wish to embody within the scope of the patent warranted hereon all such modifications as reasonably and properly come within the scope of my contribution to the art.

I claim as my invention:

1. A cassette receptacle for x-ray film cassettes including a radiation detector comprising:
    a one-piece drawn plastic part having molded parts which project inwardly proceeding from a floor of the cassette receptacle to define a space for the radiation detector;
    at least one depression in at least one molded part for receiving a cable of said detector;
        projections provided at an upper side of said receptable to engage over a cassette placed above said detector;
        at least one opening in said floor of said receptacle to provide manual engagement with said cassette to permit removal of said cassette; and
    at least one fitting slot in a longitudinal side of said receptacle to permit the insertion of said radiation detector.

2. A cassette receptacle according to claim 1, wherein said plastic part accepting the radiation detector is a deep drawn molded part.

3. A cassette receptacle according to claim 1, wherein said molded parts define step-shaped edges which allow the insertion of the rectangular radiation detector in a longitudinal or transverse orientation relative to said receptable.

4. A cassette receptable for x-ray film cassettes including a radiation detector comprising:
    a one-piece drawn plastic part having side walls and a bottom wall, said bottom wall having molded portions which project upwardly to define a space therebetween for the radiation detector;
    at least one depression in at least one of said molded portions for receiving a cable of said detector;
    projections extending inwardly from at least two opposite side walls to engage over a cassette placed above said detector;
    at least one opening in the bottom wall to provide manual engagement with said cassette to permit removal of said cassette; and at least one fitting slot in one of said side walls of said receptable to permit the insertion of said radiation detector.

5. A cassette receptacle according to claim 1, wherein said drawn plastic part has said molded parts shaped to at least the corner contours of the radiation detector to receive and hold the radiation detector in a fixed, predetermined location within said receptacle.

* * * * *